(12) United States Patent
Tijanic et al.

(10) Patent No.: US 7,462,586 B2
(45) Date of Patent: Dec. 9, 2008

(54) METHOD OF CLEANING DENTAL AND MEDICAL INSTRUMENTS USING ANTI CORROSION DETERGENT COMPOSITIONS

(75) Inventors: Veso Tijanic, Woodbridge (CA); Bhupinder Bharaj, Markham (CA); Edgar Joel Acosta Zara, Toronto (CA); Navid Omidbakhsh, Mississauga (CA)

(73) Assignee: Scican Ltd., Ontario (CA)

( * ) Notice: Subject to any disclaimer, the term of this patent is extended or adjusted under 35 U.S.C. 154(b) by 0 days.

(21) Appl. No.: 11/353,049

(22) Filed: Feb. 14, 2006

(65) Prior Publication Data

US 2006/0194706 A1   Aug. 31, 2006

Related U.S. Application Data

(60) Provisional application No. 60/652,701, filed on Feb. 15, 2005.

(51) Int. Cl.
   *C11D 1/825* (2006.01)
(52) U.S. Cl. .................................................... 510/161
(58) Field of Classification Search ..................... 134/2; 510/161
   See application file for complete search history.

(56) References Cited

U.S. PATENT DOCUMENTS

| | | | | |
|---|---|---|---|---|
| 5,234,832 A | * | 8/1993 | Disch et al. | 435/264 |
| 5,589,099 A | * | 12/1996 | Baum | 510/514 |
| 5,645,755 A | * | 7/1997 | Wiesenfeld et al. | 252/70 |
| 5,712,236 A | | 1/1998 | Bolkan et al. | |
| 5,814,588 A | * | 9/1998 | Cala et al. | 510/175 |
| 6,315,835 B1 | | 11/2001 | Kerobo et al. | |
| 2002/0173437 A1 | * | 11/2002 | Rabon et al. | 510/161 |

FOREIGN PATENT DOCUMENTS

| | | |
|---|---|---|
| CA | 2305290 | 4/1999 |
| CA | 2313870 | 1/2001 |
| CA | 2398942 | 8/2001 |
| WO | WO 97/05222 | 2/1997 |
| WO | WO 97/34711 | 9/1997 |
| WO | WO 03/042762 | 5/2003 |

* cited by examiner

*Primary Examiner*—John R Hardee
(74) *Attorney, Agent, or Firm*—Clark & Brody

(57) ABSTRACT

A novel method for cleaning dental and medical instruments is disclosed, in which a cleaning solution including a low-residue corrosion inhibitor is used not only in a wash stage of the cleaning cycle, but also in at least one subsequent rinse cycle, to optimize both cleaning and rust prevention. A novel cleaning solution particularly suited to this method has a neutral to alkaline pH and comprises in aqueous solution a low-foaming surfactant and a corrosion inhibitor selected from the group of C4-C16 alkyl pyrrolidones and C1-C18 alkylamines.

6 Claims, No Drawings

METHOD OF CLEANING DENTAL AND MEDICAL INSTRUMENTS USING ANTI CORROSION DETERGENT COMPOSITIONS

RELATED APPLICATION

This application replaces and claims priority from U.S. provisional patent application No. 60/652,701 filed on Feb. 15, 2005 and entitled METHODS FOR DENTAL AND MEDICAL INSTRUMENT CORROSION PREVENTION.

BACKGROUND OF THE INVENTION

The present invention relates generally to methods for cleaning dental and medical instruments. In particular, the invention is according to one aspect directed to a novel process of carrying out the cleaning of dental and surgical instruments to optimize both corrosion protection and cleaning efficiency.

According to another aspect, the present invention is directed to novel detergent-anti corrosion compositions for medical and surgical instruments which are particularly adapted for use in the cleaning process of the present invention.

Despite being fabricated from stainless steel, dental and medical instruments are subject to corrosion during the maintenance cycle (washing, disinfection, sterilization). Dental instruments are typically more susceptible to corrosion, owing to their higher carbon content. In order to achieve desired instrument characteristics such as surface hardness and durability, instrument manufacturers often resort to manufacturing processes such as heat treatment which also have the undesirable effect of compromising the resistance of the instruments to corrosion. In order to reduce the magnitude and rate of the process of corrosion, or even to prevent it from taking place altogether, some active corrosion protection steps have to be taken.

It has been known that in some cases, even just prolonged exposure to fresh water would start corrosion on the instrument surface. Some detergents developed for cleaning of medical instruments contain rust inhibitors. The action of these inhibitors is limited to the washing stage of the cleaning cycle, the only stage during which the detergent is used, conventionally. This typically excludes all rinsing stages and the final air-drying stage of the cleaning cycle. To cover these stages as well, different sets of chemicals are often used. These chemicals are known as rinse aids with rust inhibitors. A rinse aid serves the dual purpose of (i) changing rinse water properties in order to aid in the drying of the instruments, and (ii) improving protection against rust. Surgical milk products can also be used to protect the instruments' surface from corrosion after a rinse stage.

Such processes create the need for a number of different chemicals to be used during the wash cycle. The cost of individual chemicals, handling and chemical dispensing systems makes the cleaning process expensive and complex.

A typical cycle for cleaning medical instruments consists of a number of consecutive stages: pre-wash, wash, rinses (usually two) and drying. The pre-wash stage is used to dissolve blood on the instruments and it is run with cold water so as to prevent blood coagulation. The wash part of the cycle is run with hot/warm water and a detergent. Wash time, water temperature and detergent are matched according to requirements. A number of rinses are used to remove soil dissolved in the wash stage as well as the remaining detergent.

A number of detergents enhanced with rust inhibitors have been developed specifically for use in ultrasonic washers, where rinsing of the instruments is not recommended in order to maintain the presence of the detergent on the instruments' surface. An example is afforded by the Ultrasonic Solution made by Health Sonics Corporation. The rust inhibitors remain on the surface of the instruments after the cleaning cycle is finished. This rust protection has a time-limited action and will evaporate from the surface or get burned off during the usual high-temperature sterilization process, so that essentially no residuals are left on the surface of the instrument when it is next used on a patient.

Unfortunately, by avoiding the rinse stage in order to obtain the maximum protective effect of such rust inhibitors, the cleanliness of the instruments can be compromised. The very purpose of a rinse stage is to rinse away dirt loosened and dissolved in the wash stage, and to flush it out together with used detergent.

SUMMARY OF THE INVENTION

The term "no-rinse anti-corrosion detergent" will be used to refer to detergents enhanced with rust inhibitors that remain on the surface of instruments after the cleaning cycle is finished, where the rust protection has a time-limited action and will evaporate from the surface or get burned off during a high-temperature sterilization process, so that essentially no residuals will be present on the surface of the instrument when it is used on a patient.

We have found that a number of such no-rinse anti-corrosion detergents can, in fact, effectively be used in a washing cycle which includes wash, rinse and drying stages (as in a process-controlled spray washer) to protect against corrosion, but without compromising cleaning effectiveness. The detergent is used during the wash stage of the cleaning cycle to clean and prevent corrosion (as it is when used in an ultrasonic washer), but is also added, at lower concentrations, to subsequent rinsing stages, particularly the last rinse stage. This maintains a high level of corrosion protection without foregoing the rinsing which is essential for proper cleaning. This new method of cleaning instruments, in which at least the final rinse contains detergent, eliminates the need for multiple chemicals (cleaner, rinse aid, surgical milk).

We have also developed a family of specially formulated anti-corrosion detergent compositions containing a low foaming surfactant and alkyl pyrrolidones or certain alkyl amines, which afford corrosion control during washing/disinfection of medical instruments in automated washing systems having programmed wash and rinse stages.

DESCRIPTION OF THE INVENTION

As noted above, we have discovered that suitable detergents enhanced with rust inhibitors (chiefly, those for which the rust protection has a time-limited action and evaporates from the surface or is readily burned off during subsequent heat sterilization) can be utilized in a process-controlled spray washer, not only during the wash stage but in one or more rinse stages to optimize both cleaning and corrosion prevention. Such instrument washers are exemplified by the HYDRIM (trademark) instrument washers made by SciCan.

Table 1 illustrates a typical detergent dosing schedule for the pre-wash, wash and second rinse stages in the cleaning cycles of a HYDRIM C51W Instrument washer manufactured by SciCan. For this machine, the total water volume through the cleaning cycle is 3 L. The total volume of detergent dispensed in the prewash, wash and $2^{nd}$ rinse stages are, respectively, 5.7 mL, 37 mL, and 11.37 mL.

TABLE 1

| | DETERGENT DOSING (in ml) Hydrim C51W | | | |
|---|---|---|---|---|
| | PREWASH | WASH | | 2$^{ND}$ RINSE |
| CYCLE | Start of Prewash Stage | Start of Wash Stage | At 45° C. | Start of 2$^{nd}$ Rinse |
| P1 (NORMAL) | 5.7 | 18.5 | 18.5 | 11.37 |
| P2 (HEAVY) | 5.7 | 18.5 | 18.5 | 11.37 |

Either of two cleaning programs (cycles) may be selected by the user. That designated P1 (normal) runs from pre-wash through a second rinse for about five minutes while the P2 (heavy) cycle takes about nine minutes. In each case, a low concentration (e.g. 30% of full strength) of an anti-corrosion detergent composition is added at the beginning of the pre-wash stage.

A higher level of the cleaning composition (full detergent concentration) is added at the beginning of the wash stage and again when the heating of the wash water has reached 45° C., to provide cleaning properties as well as corrosion protection. The temperature range over which the HYDRIM machine operates is from room temperature up to about 70 deg C. This detergent can also be used in washers/disinfectors which attain temperatures of 93 deg C.

A first rinse is run without any detergent. It is a short phase, the residual detergent from the wash phase still protecting the instruments.

The second (and any subsequent) rinse is run with a reduced concentration of detergent (e.g. 30% of full strength). Here the detergent is used for corrosion protection and as a rinsing aid. The detergent is changing the rinse water surface tension to increase water removal (shedding) from the surface. The chemicals from the detergent also protect instruments from corrosion while wet and during the drying cycle. The dry surface left behind is visually clean with no harmful residuals. Detected residuals are at a level below than $23 \times 10^{-3}$ μg/mm$^2$ of instrument surface, a result which is comparable to that obtained when any other rinse aid generally used. The residuals are invisible and do not adversely affect the instrument appearance, performance, useful life or maintenance cycle.

A number of commercially available no-rinse anti-corrosion detergents intended for use in ultrasonic cleaners may advantageously be used according to the method of the invention. That is, they may also be added at stages subsequent to the washing stage of a cleaning cycle. However, we have developed a specially formulated low foaming corrosion protection cleaning concentrate solution, containing a low-foaming surfactant and an alkyl pyrrolidone or alkylamine, which affords superior cleaning and corrosion inhibition properties.

It was found that cleaning concentrates according to the invention and diluted solutions, containing at least 0.005% of a low foaming surfactant and at least 0.005% of a C4-C16 alkyl pyrrolidone or C1-C18 alkylamine, exhibit surprisingly superior cleaning/corrosion inhibition properties, particularly in the cleaning of metal dental instruments. Certain such instruments often become rusted after cleaning and rinsing, but formulations according to the present invention prevent rusting and corrosion.

The cleaning concentrate solution of the invention has a neutral to alkaline pH, preferably from 7 to 12. Throughout this specification the concentrations of components in the aqueous cleaning compositions is stated in weight percent. The active components of low foam, corrosion protection cleaning solutions according to the invention are as follows:

(a) a low foaming surfactant from about 0.005 to 10% of the formulation selected from polyoxyethylene/polyoxypropylene block co-polymers, having a polyoxypropylene molecular weight of from about 1500 to 8500, of which less than about 30% of the total molecular weight is due to the polyoxypropylene;

(b) as a corrosion inhibiting component, from about 0.005 to 10% of a compound selected from C4-C16 alkyl pyrrolidones or C1-C18 alkylamines;

(c) at least one builder from about 0.01 to 15% of the formula selected from the group of phosphonic acids such as 1-hydroxyethylidiene, 1,1 diphosphonic acid, amino tri (methylene phosphonic acid), diethylenetriaminepenta (methylene phosphonic acid), 2-hydroxyethylimoino bis (methylene phosphonic acid), ethylene diamine tetra (methylene phosphonic acid), EDTA (ethylenediaminetetraacetic acid), DTPA (diethylenetriaminepentaacetic acid), HEDTA (N-(hydroxyethyl)-ethylenediaminetriacetic acid), NTA (nitrilotriacetic acid), 2-hydroxyethyliminodiacetic acid, sodium or potassium tripolyphosphate, citric acid, sodium tetraphosphate, sodium hexametaphosphate, and mixtures thereof; and (d) at least one hydrotrope from about 0% to 20% of the formula selected from the group of sodium xylene sulfonate, sodium cumene sulfonate, C6-C18 alkyl sulphonic acids and salts thereof, C6-C20 alkylpolyglycosides, and C6-C16 diphenyloxide disulphonate.

The term "builder" is commonly used in the field of detergent formulation to refer to a molecule that can trap and remove multivalent cations like calcium and magnesium from the water. Such cations tend to precipitate the surfactant, forming undesirable scum or scale.

"Hydrotopes" are compounds used to increase the solubility of surfactants in aqueous solutions. Their use is described in textbooks and literature in this field, for example, *The Book of Surfactants and Interfacial Phenomena* by Milton Rosen.

Although a number of alkyl pyrrolidones have been used as surfactants, their effective role as corrosion inhibitors is novel and surprising. It is speculated that this may stem from the ability of C4-C16 alkyl pyrrolidones to become zwitterions in solution, with an ability to absorb to positively or negatively charged metallic surfaces, thereby providing an homogeneous protection against corrosion.

As for C1-C18 alkylamines, at neutral or slightly alkaline pH these compounds ionize to a quaternary ammonium form, that positive ion can adsorb to negatively-charged metal surfaces, again promoting the inhibition of corrosion.

Compositions according to the present invention may optionally contain as additional ingredients:

at least one solvent from about 0.001 to 20% of the formula selected from the group of glycols, glycol ethers, C1 to C6 linear or branched alcohols, and aromatic alcohols;

at least one pH buffer from about 0.001 to 10% of the formula selected from boric acid, citric acid, phosphoric acid, and salts thereof;

at least one further surfactant from 0.01 to 10% chosen from non-ionics, anionics, amphoterics and cationics; and at least one corrosion inhibitor from about 0.001% to 10% of the formula selected from the group of molybdates (e.g. sodium molybdate), nitrites (e.g. sodium nitrite), triazoles (e.g. 1,2,3 benzatriazole), gluconates and carboxylic acids.

A set of washing tests was performed on stainless steel rods having high (min 0.15%) carbon content. This material had been heat treated to reduce corrosion resistance. The surfaces of these rods where inspected for the appearance of "rusting".

While conventional no-rinse anti-corrosion detergents showed more than 25% of the surface covered with rust/corrosion, applicant's formulations of Table 2 all exhibited less than 5% corrosion coverage; the currently most preferred embodiment of the anti-corrosion detergent composition of the invention, set out in Table 3, produced no visually detectable rusting or corrosion on the surface of the test steel rods.

It will be understood by those skilled in the art that various modifications may be made in the methods and compositions described above without departing from the spirit and scope of the present invention. Accordingly, it is intended that the specific embodiments described herein be understood as illustrative only, and that the invention is limited only by the claims appended hereto.

TABLE 2

| Raw Material | 4472 % w/w | 4473 % w/w | 4474 % w/w | 4475 % w/w | 4608 % w/w | 4673 % w/w | 4677 % w/w | 4679 % w/w | 4680 % w/w | 4690 % w/w |
|---|---|---|---|---|---|---|---|---|---|---|
| DI water[1] | | | qs to 100 | | 50.60 | 45.60 | 47.30 | 58.30 | 62.30 | 33.24 |
| Dequest 2010[2] | | 8.00 | | | 8.00 | 8.00 | 8.00 | 8.00 | 8.00 | 12.80 |
| KOH (45%)[3] | | 11.50 | | | 11.50 | 11.50 | 11.50 | 10.50 | 9.00 | 16.80 |
| Propylene glycol[4] | | 7.00 | | | 8.00 | 12.00 | 12.00 | 10.00 | 9.50 | 16.00 |
| Sodium Xylene sulfonate[5] | | 8.40 | | | | | | | | |
| Pluronic 17R2[6] | | 0.05 | | | 0.50 | | 0.70 | 0.50 | 0.50 | 0.80 |
| Bioterge PAS-8S[7] | | 1.40 | | | 1.40 | 1.40 | | | | |
| Cobratec 35 G[8] | | 3.50 | | | | | | | | |
| Sodium molybdate[9] | | 1.50 | | | 1.50 | 1.50 | 1.50 | | | |
| Boric acid[10] | | 2 | | | 2.00 | 2.00 | 2.00 | 0.20 | 0.20 | 0.20 |
| Octylamine[11] | 1 | 0 | 0 | 0 | | | | | | |
| Surfadone LP-100[12] | 0 | 2 | 0 | 0 | 2.00 | 4.00 | 2.00 | 2.00 | 2.00 | 3.20 |
| Tri Ethanol Amine[13] | 0 | 0 | 5 | 0 | | | | | | |
| SXS[14] | | | | | 14.50 | 14.00 | 14.00 | 10.00 | 8.00 | 16.00 |
| Ethox 2400[15] | | | | | | | 1.00 | 0.50 | 0.50 | 0.96 |
| Total | 100 | 100 | 100 | 100 | 100 | 100 | 100 | 100 | 100 | 100 |

Notes:
[1] carrier
[2] 1-hydroxyethylidiene, 1,1 diphosphonic acid (builder)
[3] Potassium hydroxide (pH adjuster)
[4] solvent
[5] hydrotrope
[6] TM of BASF for polyoxyetheylene/polyoxypropylene co-polymer (defoamer)
[7] TM of Stepan for octyl sulfonate (anionic surfactant)
[8] 1,2,3 benzotriazole (anti corrosion agent for copper)
[9] corrosion inhibitor
[10] non-toxic pH buffer
[11] corrosion inhibitor
[12] TM of ISP for N-octyl-2-pyrrolidone (corrosion inhibitor)
[13] corrosion inhibitor and pH adjuster
[14] brand of Stepan for sodium xylene sulfonate (hydrotrope)
[15] TM of Ethox for ethyleneoxide/propyleneoxide co-polymer (non-ionic surfactant)

TABLE 3

| Raw Material | Chemical name | Source/Supplier | % w/w |
|---|---|---|---|
| DI water | Carrier | | 50.14 |
| Dequest 2010 (60%) | 1-hydroxyethylidiene, 1,1 diphosphonic acid | Solutia | 10.50 |
| Propylene glycol | Solvent | | 5.00 |
| Boric acid | PH buffer | Borax | 0.20 |
| SXS (40%) | Sodium xylene sulfonate (hydrotrope) | Stepan | 16.00 |
| KOH (45%) | Potassium hydroxide (pH adjuster) | | 12.80 |
| Ethox 2400 | Alcohol ethoxylate (non-ionic surfactant) | Ethox co. | 0.96 |
| Surfodone LP 100 | N-octyl-2-pyrrolidone (cationic surfactant) | ISP corporation | 3.20 |
| Dehypon LS 36 | Alcohol C12-C14 EO/PO (non-ionic surfactant-defoamer) | Cognis | 0.60 |
| Dehypon LS 54 | Alcohol C12-C14 EO/PO (non-ionic surfactant-defoamer) | Cognis | 0.60 |
| Total | | | 100 |

We claim:

1. A method of cleaning metal medical and dental instruments to remove contaminants therefrom and inhibit corrosion, comprising:

(a) in a wash stage, washing the instruments in an aqueous wash solution containing a detergent composition including a low-residue corrosion inhibitor in accordance with a predetermined cleaning program to loosen or dissolve substantially all contaminants expected to be on said instruments, then draining the aqueous wash solution from the instruments; then (b) submitting the instruments to at least one stage of rinsing to remove said contaminants and said aqueous wash solution remaining after said wash stage by using an aqueous rinse liquid, said aqueous rinse liquid being substantially free of said aqueous wash solution and including a selected concentration of said detergent to flush said contaminants and said aqueous wash solution from said instruments in at least the final rinse stage.

2. A method according to claim 1, wherein said detergent composition comprises, in aqueous solution:
   (a) from 0.005 to 10% of a low-foaming surfactant;
   (b) from 0.005 to 10% of a corrosion inhibiting compound selected from C4-C16 alkyl pyrrolidones and C1-C18 alkylamines;
   (c) from 0.01 to 15% of a builder compound to prevent the formation of precipitates by reaction of metal ions in the aqueous solution with said surfactant; and
   (d) from 0% to 20% of a hydrotrope, wherein the pH of said anti-corrosion detergent composition is neutral to alkaline.

3. A method according to claim 1, wherein said detergent composition comprises, in aqueous solution:
   (a) from 0.005 to 10% of a low-foaming surfactant selected from the group consisting of polyoxyethylene/polyoxypropylene block co-polymers, having a polyoxypropylene molecular weight of from about 1500 to 8500, of which less than about 30% of the total molecular weight is due to the polyoxypropylene;
   (b) from 0.005 to 10% of a corrosion inhibiting compound selected from C4-C16 alkyl pyrrolidones or C1-C18 alkylamines;
   (c) a builder compound to prevent the formation of precipitates by reaction of a metal in the aqueous solution with the surfactant, selected from the group consisting of 1-hydroxyethylidiene, 1.1 diphosphonic acid, amino tri (methylene phosphonic acid), diethylenetriaminepenta (methylene phosphonic acid), 2-hydroxyethylimino bis (methylene phosphonic acid), ethylene diamine tetra (methylene phosphonic acid), EDTA (ethylenediaminetetraacetic acid), DTPA (diethylenetriaminepentaacetic acid), HEDTA (N-(hydroxyethyl)-ethylenediaminetriacetic acid), NTA (nitrilotriacetic acid), 2-hydroxyethyliminodiacetic acid, sodium or potassium tripolyphosphate, citric acid, sodium tetraphosphate, sodium hexametaphosphate, and mixtures thereof; and
   (d) from 0% to 20% of a hydrotrope selected from the group consisting of sodium xylene sulfonate, sodium cumene sulfonate, C6-18 alkyl sulphonic acids and salts thereof C6-C20 alkylpolyglocosides, and C6-C16 diphenyloxide disulphonate, wherein the pH of the aqueous solution is from 7 to 12.

4. A method according to claim 1, comprising a pre-wash stage using an aqueous solution containing said detergent at a lower concentration than is present in said wash stage.

5. A method according to claim 4, wherein said detergent composition comprises, in aqueous solution:
   (a) from 0.005 to 10% of a low-foaming surfactant;
   (b) from 0.005 to 10% of a corrosion inhibiting compound selected from C4-C16 alkyl pyrrolidones and C1-C18 alkylamines;
   (c) from 0.01 to 15% of a builder compound to prevent the formation of precipitates by reaction of metal ions in the aqueous solution with said surfactant; and
   (d) from 0% to 20% of a hydrotrope, wherein the pH of said anti-corrosion detergent composition is neutral to alkaline.

6. A method according to claim 4, wherein said detergent composition comprises, in aqueous solution:
   (a) from 0.005 to 10% of a low-foaming surfactant selected from the group consisting of polyoxyethylene/polyoxypropylene block co-polymers, having a polyoxypropylene molecular weight of from about 1500 to 8500, of which less than about 30% of the total molecular weight is due to the polyoxypropylene;
   (b) from 0.005 to 10% of a corrosion inhibiting compound selected from C4-C16 alkyl pyrrolidones or C1-C18 alkylamines;
   (c) a builder compound to prevent the formation of precipitates by reaction of a metal in the aqueous solution with the surfactant, selected from the group consisting of 1-hydroxyethylidiene, 1,1 diphosphonic acid, amino tri (methylene phosphonic acid), diethylenetriaminepenta (methylene phosphonic acid), 2-hydroxyethylimino bis (methylene phosphonic acid), ethylene diamine tetra (methylene phosphonic acid), EDTA (ethylenediaminetetraacetic acid), DTPA (diethylenetriaminepentascetic acid). HEDTA (N-(hydroxyethyl)-ethylenediaminetriacetic acid), NTA (nitrilotriacetic acid), 2 hydroxyethyliminodiacetic acid, sodium or potassium tripolyphosphate, citric acid, sodium tetraphosphate, sodium hexametaphosphate, and mixtures thereof; and
   (d) from 0% to 20% of a hydrotrope selected from the group consisting of sodium xylene sulfonate, sodium cumene sulfonate, C6-18 alkyl sulphonic acids and salts thereof, C6-C20 alkylpolyglocosides, and C6-C16 dipheriyloxide disulphonate, wherein the pH of the aqueous solution is from 7 to 12.

* * * * *